United States Patent
Hasslacher et al.

(10) Patent No.: US 10,036,002 B2
(45) Date of Patent: Jul. 31, 2018

(54) FACTOR X ACTIVATION

(71) Applicants: Baxalta Incorporated, Bannockburn, IL (US); Baxalta GmbH, Glattpark (Opfikon) (CH)

(72) Inventors: Meinhard Hasslacher, Vienna (AT); Thomas Gatternig, Vienna (AT); Christian Fiedler, Vienna (AT); Ernst Böhm, Vienna (AT); Michael Dockal, Vienna (AT); Franziska Horling, Gänserndorf (AT)

(73) Assignees: Baxalta GmbH, Zug (CH); Baxalta Incorporated, Bannockburn, IL (US)

( * ) Notice: Subject to any disclaimer, the term of this patent is extended or adjusted under 35 U.S.C. 154(b) by 0 days.

(21) Appl. No.: 14/824,870

(22) Filed: Aug. 12, 2015

(65) Prior Publication Data

US 2016/0046922 A1 Feb. 18, 2016

Related U.S. Application Data

(60) Provisional application No. 62/036,402, filed on Aug. 12, 2014.

(51) Int. Cl.
*C12N 9/00* (2006.01)
*C12N 9/64* (2006.01)

(52) U.S. Cl.
CPC .... *C12N 9/6432* (2013.01); *C12Y 304/21006* (2013.01)

(58) Field of Classification Search
None
See application file for complete search history.

(56) References Cited

U.S. PATENT DOCUMENTS

| | | | | |
|---|---|---|---|---|
| 6,013,620 A | * | 1/2000 | Turecek | A61K 38/4846 424/530 |
| 2014/0302591 A1 | * | 10/2014 | Mitterer | C07K 1/18 435/226 |
| 2014/0302592 A1 | * | 10/2014 | Mitterer | C07K 1/18 435/226 |
| 2016/0039869 A1 | * | 2/2016 | Mitterer | C07K 14/745 435/226 |

FOREIGN PATENT DOCUMENTS

| | | |
|---|---|---|
| WO | 2008/145989 A1 | 12/2008 |
| WO | 2014/140289 A1 | 9/2014 |

OTHER PUBLICATIONS

Fujikawa et al., Biochemistry vol. 11, No. 26: 4882-4891 (1972) (Year: 1972).*
Himmelspach et al., Recombinant human factor X: high yield expression and the role of Furin in proteolytic maturation in vivo and in vitro. Thrombosis Research, vol. 97, pp. 51-67 (2000).
International Application No. PCT/US2015/044863 filed on Aug. 12, 2015.
International Search Report and Written Opinion for International Application No. PCT/US2015/044863 filed on Aug. 12, 2015.
Pedersen et al., Autoactivation of human recombinant coagulation factor VII. Biochemistry, vol. 28, No. 24, pp. 9331-9336 (1989).

* cited by examiner

*Primary Examiner* — Anand U Desai
(74) *Attorney, Agent, or Firm* — Wolf, Greenfield & Sacks, P.C.

(57) ABSTRACT

Methods and systems for activating Factor X are disclosed.

21 Claims, 1 Drawing Sheet

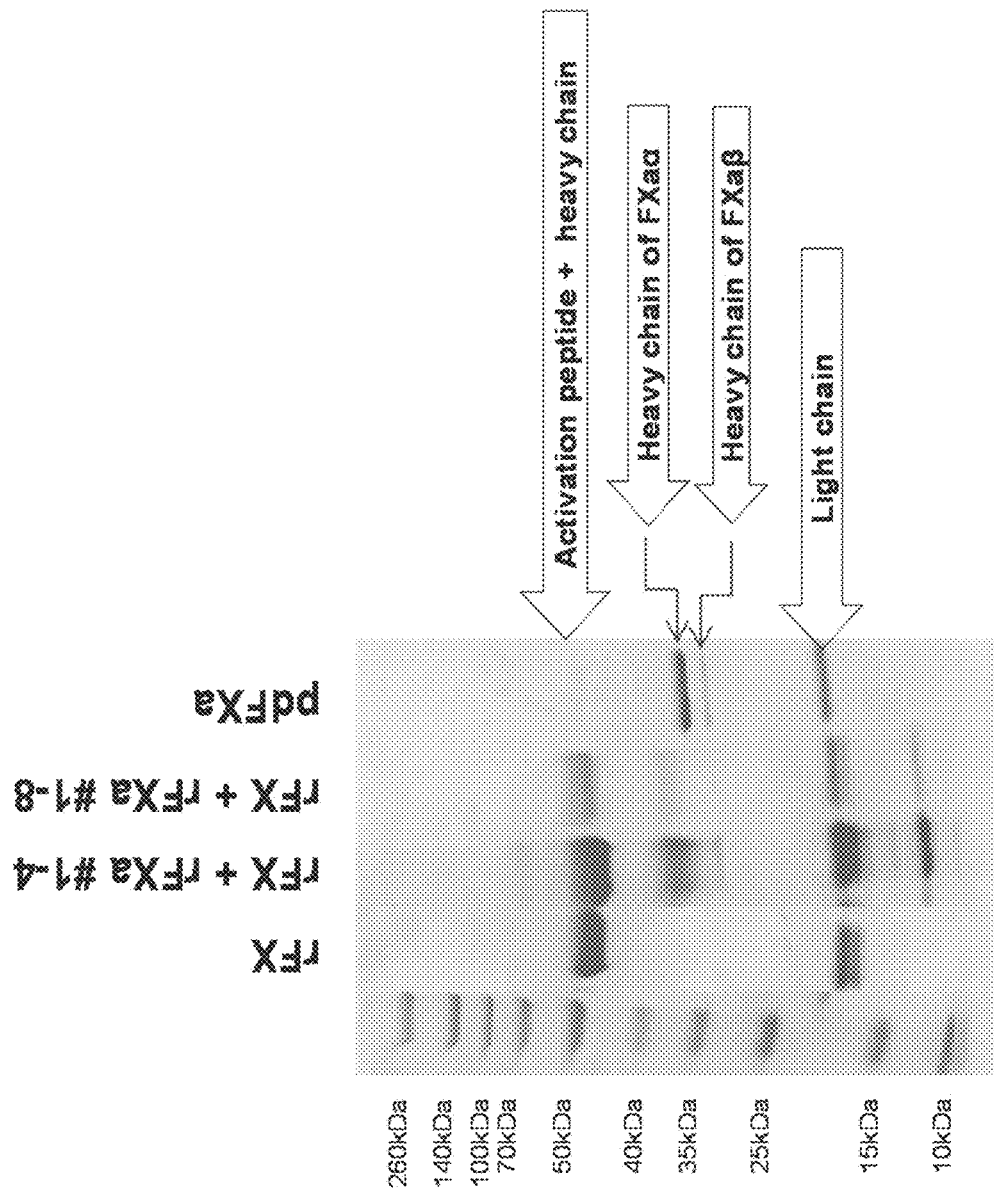

FACTOR X ACTIVATION

CROSS REFERENCE TO RELATED APPLICATIONS

The present application claims the benefit under 35 U.S.C. 119(e) to U.S. Provisional Patent Application 62/036,402, filed Aug. 12, 2014, the entire contents of which are incorporated by reference herein.

FIELD

The present disclosure relates to methods and systems for activating Factor X.

BACKGROUND

Coagulation Factor X, also known as FX, F10, Eponym Stuart-Prower factor, and thrombokinase, is a vitamin K-dependent plasma protease that activates thrombin. Initially synthesized in the liver as a single-chain precursor, FX is activated by both intrinsic and extrinsic pathways to form activated FX (FXa), consisting of disulfide bond-linked light and heavy chains. The light chain contains γ-carboxyglutamic acid (Gla) domains and two epidermal growth factor-like (EGF-like) domains, while the heavy chain corresponds to the serine protease domain. FXa contributes to the action of prothrombin complex concentrate and has been identified as an active component in factor eight bypassing activity (FEIBA). FEIBA can be used to treat hemophilia patients who develop inhibitory antibodies against FVIII or FIX.

While FX can be purified from human plasma or produced recombinantly, only in its activated state (FXa) does it affect the blood coagulation process. This activation results from cleavage of the Arg52-Ile53 peptide bond in the heavy chain of FX, releasing the activation peptide. Standard methods of FX activation typically employ exogenous agents such as proteases.

SUMMARY

Aspects disclosed herein include methods for activating Factor X (FX) without the addition of exogenous agents. In an embodiment FX is activated through associating the FX with a chromatography resin.

Further aspects include systems for activating FX. In an embodiment the system includes FX in a liquid medium and an anion exchange chromatography resin. In an embodiment the liquid medium is aqueous.

Aspects include eluting the activated FX 2 hours after beginning the step of loading the FX on to the chromatography resin.

Aspects include eluting the activated FX 5 hours after beginning the step of loading the FX on to the chromatography resin.

Aspects include eluting the activated FX 10 hours after beginning the step of loading the FX on to the chromatography resin.

Aspects include eluting the activated FX 20 hours after beginning the step of loading the FX on to the chromatography resin.

Further aspects disclosed herein include binding the FX at a conductivity of 8 mS/cm or less.

Further aspects disclosed herein include binding the FX at a pH of between 8 and 10.

Further aspects disclosed herein include loading the FX at greater than 0.5 mg per mL of anion exchange resin. In certain aspects the binding and eluting steps are performed at a temperature of greater than 8° C.

Methods disclosed herein include an elution buffer that comprises a divalent cation or a counter-ion. In certain methods the counter-ion is at least one of chloride, acetate, citrate, sulfate, or phosphate. In certain methods disclosed herein the concentration of the divalent cation or counter-ion or both in the elution buffer increases over time.

Aspects disclosed herein include an elution buffer with a conductivity between 1 and 100 mS/cm at 25° C. Further aspects include ion exchange ligands that are at least one of quaternary ammonium [Q], diethylaminoethyl [DEAE], diethylaminopropyl [ANX], or primary amine. Further aspects include on exchange materials that are a matrix derived from at least one of polystyrene, polymethylmetaacrylate, polyvinylbenzene, polyvinyl pyridine, cross-linked poly(styrene-divinylbenzene), sepharose, and cross linked agarose. In certain aspects, the ion exchange material is an anion exchange material.

In embodiments the ion exchange material comprises at least one of POROS® 50 HQ (strong anion exchange media based on quarternized polyetheyleneimine functional group; Life Technologies), POROS® PI (weak anion exchange media based on polyetheyleneimine functional group; Life Technologies), POROS® D (weak anion exchange media; Life Technologies), Q SEPHAROSE® FF (Q Sepharose Fast Flow, crosslinked 6% agarose beads, with quaternary ammonium strong anion exchange groups, GE Healthcare Life Sciences), Q SEPHAROSE® HP (crosslinked agarose beads with a mean diameter of 34 μm, modified with quaternary strong anion exchange groups, GE Healthcare Life Sciences), ESHMUNO® Q (strong anion exchanger with trimethylammoniummethyl function groups cross-linked to surface grafted rigid polyvinyl ether hydrophilic polymer, Merck Millipore), FRACTOGEL® TMAE (strong anion exhanger synthetic of methacrylate based polymeric beads with trimethylammoniummethyl function groups, EMD Millipore), FRACTOGEL® EMD DEAE (weak anion exhanger synthetic of methacrylate based polymeric beads with DEAE function groups, EMD Millipore), FRACTOGEL® EMD DMAE (weak anion exhanger synthetic of methacrylate based polymeric beads with dimethylaminoethanol function groups, EMD Millipore), Q Ceramic HYPERD® F (high-capacity hydrogel polymerized within the gigapores of a rigid ceramic bead with quaternary ammonium functional groups, Pall Corporation), MUSTANG® Q (anion-exchange support with pendant quaternary amine functional groups in a cross-linked polymeric coating on a 0.8 micron pore-size membrane, Pall Corporation), DEAE SEPHAROSE® Fast Flow (crosslinked 6% agarose beads, with DEAE weak anion exchange groups, GE Healthcare Life Sciences), ANX SEPHAROSE® 4 Fast Flow (highly cross-linked, 4% agarose derivative with weak anion exchange tertiary amine groups, GE Healthcare Life Sciences), Q SEPHAROSE® XL (highly cross-linked, bead formed 6% agarose matrix with dextran chains are covalently coupled to the agarose matrix and modified with quaternary ammonium strong anion exchange groups, GE Healthcare Life Sciences), Q SEPHAROSE® big beads (crosslinked agarose beads [100-300 μm] modified with sulphonate strong cation exchange groups, GE Healthcare Life Sciences), DEAE SEPHADEX® (weak anion exchanger of cross-linked dextran matrix with DEAE functional groups, GE Healthcare Life Sciences), QAE SEPHADEX® (strong anion exchanger of cross-linked dextran matrix with diethyl-(2-hydroxy-propyl)aminoethyl functional groups, GE Healthcare Life Sciences), SOURCE™

150 (strong anion exchanger based on 15 μm monosized rigid polystyrene/divinyl benzene polymer matrix modified with quaternary ammonium functional groups, GE Healthcare Life Sciences), Source 30Q (strong anion exchanger based on 30 μm monosized rigid polystyrene/divinyl benzene polymer matrix modified with quaternary ammonium functional groups, GE Healthcare Life Sciences), Capto Q (rigid, high-flow agarose matrix modified with dextran surface extenders and a strong quaternary ammonium anion exchanger, GE Healthcare Life Sciences), Capto DEAE (rigid, high-flow agarose matrix modified with dextran surface extenders and a weak DEAE anion exchanger, GE Healthcare Life Sciences), Mono Q (strong anion exchanger of Monobeads conjugated to strong quaternary ammonium anion exchanger, GE Healthcare Life Sciences), TOYOPEARL® Super Q (hydroxylated metacrylate polymer resin with strong anion exchanger functional group, Tosoh Bioscience), TOYOPEARL® DEAE (hydroxylated metacrylate polymer resin with weak anion exchanger functional group, Tosoh Bioscience), TOYOPEARL® QAE (hydroxylated metacrylate polymer resin with strong anion exchanger functional group, Tosoh Bioscience), TOYOPEARL® Q (hydroxylated metacrylate polymer resin with strong anion exchanger functional group, Tosoh Bioscience), TOYOPEARL® GigaCap Q (hydroxylated metacrylate polymer resin modified to provide a higher number of anionic binding sites with strong anion exchanger functional group, Tosoh Bioscience), TSKgel® SuperQ (hydroxylated metacrylate polymer resin with a high degree of cross-linking with strong anion exchanger functional group, Tosoh Bioscience), TSKgel® DEAE (hydroxylated metacrylate polymer resin with a high degree of cross-linking with weak anion exchanger functional group, Tosoh Bioscience), MACROPREP® High (strong anion exchange resin containing methacrylate copolymer beads linked to quaternary amine functional groups, Bio-Rad), MACROPREP® DEAE (weak anion exchange resin containing methacrylate copolymer beads linked to DEAE functional groups, Bio-Rad), UNOSPHERE™ Q (strong anion exchange resin containing hydrophilic polymeric support linked to quaternary amine functional groups. Bio-Rad), and NUVIA™ (strong anion exchange resin containing hydrophilic polymeric support with surface extenders linked to quaternary amine functional groups, Bio-Rad).

BRIEF DESCRIPTION OF THE DRAWING

FIG. 1 shows an SDS-PAGE gel of FX samples: shown are the recombinant (rFX) starting material for activation (lane "rFX"), samples numbered 1-4 and 1-8 containing rFXa (activated, recombinant FX) after the activation step (lanes "rFX+rFXa #1-4" and "rFX+rFXa #1-8"), and plasma-derived (pd) EXa (lane "pdFXa"). After electrophoresis, protein bands were made visible by Coomassie staining. In the leftmost lane, a molecular weight marker is shown, Bands corresponding to FX and FXa are marked.

DETAILED DESCRIPTION

Various embodiments disclosed herein include methods for producing, purifying, storing, and activating FX. In certain embodiments the FX can be activated without the addition of exogenous agents. For example, FX can be bound to a chromatography material for a contact period to activate the FX. In an embodiment, FX can be bound to an ion-exchange resin. Following binding, the FX can be activated to produce FXa then eluted from the resin.

Throughout this specification, whole integers have been used for convenience and not intended to be limiting. For example "pH 4" can include pHs close to 4 such as but not limited to 3.8, 3.9, 4.1, 4.2, etc. The term "about" is used to indicate that these inherent small ranges and deviations from whole integers are considered part of the embodiments described and claimed herein. When a range is used, for example, and not intended as a limitation, between about 10 and 15 mS/cm, all fractions associated with the intervening values are included.

Production of FX

In certain embodiments the FX can comprise mammalian FX, for example wild-type FX or FX variants such as conservative variants of FX. A conservative variant refers to a protein or polypeptide that has at least one amino acid substituted by another amino acid or an amino acid analog that has at least one property similar to that of the original amino acid from an exemplary reference peptide. Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative substitution can be assessed by a variety of factors, such as, e.g., the physical properties of the amino acid being substituted (Table 1) or how the original amino acid would tolerate a substitution (Table 2) (IUPAC amino acid codes are used in Tables 1 and 2). The selections of which amino acid can be substituted for another amino acid in a peptide disclosed herein are known to a person of ordinary skill in the art. A conservative variant can function in substantially the same manner as the exemplary reference protein or polypeptide, and can be substituted for the exemplary reference protein or polypeptide in any aspect of the present specification.

TABLE 1

Amino Acid Properties

| Property | Amino Acids |
| --- | --- |
| Aliphatic | G, A, I, L, M, P, V |
| Aromatic | F, H, W, Y |
| C-beta branched | I, V, T |
| Hydrophobic | C, F, I, L, M, V, W |
| Small polar | D, N, P |
| Small non-polar | A, C, G, S, T |
| Large polar | E, H, K, Q, R, W, Y |
| Large non-polar | F, I, L, M, V |
| Charged | D, E, H, K, R |
| Uncharged | C, S, T |
| Negative | D, E |
| Positive | H, K, R |
| Acidic | D, E |
| Basic | K, R |
| Amide | N, Q |

TABLE 2

Amino Acid Substitutions

| Amino Acid | Favored Substitution | Neutral Substitutions | Disfavored substitution |
| --- | --- | --- | --- |
| A | G, S, T | C, E, I, K, M, L, P, Q, R, V | D, F, H, N, Y, W |
| C | F, S, Y, W | A, H, I, M, L, T, V | D, E, G, K, N, P, Q, R |
| D | E, N | G, H, K, P, Q, R, S, T | A, C, I, L, |
| E | D, K, Q | A, H, N, P, R, S, T | C, F, G, I, L, M, V, W, Y |
| F | M, L, W, Y | C, I, V | A, D, E, G, H, K, N, P, |

TABLE 2-continued

Amino Acid Substitutions

| Amino Acid | Favored Substitution | Neutral Substitutions | Disfavored substitution |
|---|---|---|---|
| G | A, S | D, K, N, P, Q, R | Q, R, S, T C, E, F, H, I, L, M, T, V, W, Y |
| H | N, Y | C, D, E, K, Q, R, S, T, W | A, F, G, I, L, M, P, V |
| I | V, L, M | A, C, T, F, Y | D, E, G, H, K, N, P, Q, R, S, W |
| K | Q, E, R | A, D, G, H, M, N, P, S, T | C, F, I, L, V, W, Y |
| L | F, I, M, V | A, C, W, Y | D, E, G, H, K, N, P, Q, R, T |
| M | F, I, L, V | A, C, R, Q, K, T, W, Y | D, E, G, H, N, P, S |
| N | D, H, S | E, G, K, Q, R, T | A, C, F, I, L, M, P, V, W, Y |
| P | — | A, D, E, G, K, Q, R, S, T | C, F, H, I, L, M, N, V, W, Y |
| Q | E, K, R | A, D, G, H, M, N, P, S, T | C, F, I, L, V, W, Y |
| R | K, Q | A, D, E, G, H, M, N, P, S, T | C, F, I, L, V, W, Y |
| S | A, N, T | C, D, E, G, H, K, P, Q, R, T | F, I, L, M, V, W, Y |
| T | S | A, C, D, E, H, I, K, M, N, P, Q, R, V | F, G, L, W, Y |
| V | I, L, M | A, C, F, T, Y | D, E, G, H, K, N, P, Q, R, S, W |
| W | F, Y | H, L, M | A, C, D, E, G, I, K, N, P, Q, R, S, T, V |
| Y | F, H, W | C, I, L, M, V | A, D, E, G, K, N, P, Q, R, S, T |

Matthew J. Betts and Robert, B. Russell, Amino Acid Properties and Consequences of Substitutions, pp. 289-316, In Bioinformatics for Geneticists, (Michael R. Barnes, Ian C. Gray, Wiley, 2003).

In various embodiments, FX can be isolated from plasma, such as from human plasma, or can be produced recombinantly, for example from mammalian tissue culture systems including human cells (such as HEK293 cells) or Baby Hamster Kidney cells (BHK cells) or Chinese Hamster Ovary (CHO cells). For example, a recombinant FX (rFX) expressing cell line can be developed in CHO cells using a plasmid vector harboring a human FX encoding cDNA and a neomycin resistance gene for antibiotic selection. rFX producing cell clones can then be isolated by limited dilution cloning. Certain embodiments can comprise "helper" proteins such as VKOR or furin. Certain embodiments disclosed herein can comprise insect cell expression systems, for example baculovirus-infected insect cell expression systems. Embodiments can comprise expression of recombinant FX in yeast cell systems. In some embodiments the FX can be expressed as a "tagged" protein, for example with a polyhistidine tag at the C-terminus. In some embodiments the produced FX can be present in the cell supernatant of the tissue culture system.

Purification/Isolation of FX

In various embodiments, FX can be isolated or purified from mammalian plasma or tissue culture cell supernatant using a number of techniques including precipitation, ultrafiltration, chromatography, etc. For example, FX can be purified using chromatography methods such as affinity chromatography, hydrophobic interaction chromatography, hydroxyapatite chromatography, ion-exchange chromatography, size-exclusion or gel-filtration chromatography, or the like. In certain embodiments the ion exchange chromatography method can comprise a strong anion exchange resin, a weak anion exchange resin, a strong cation exchange resin, a weak cation exchange resin, or the like. For example, the anion exchange resin can be Q-SEPHAROSE® (a registered trademark of G.E. Healthcare, Kentwood Mich.) Fast Flow, or the like.

In certain embodiments, purified or partially purified FX can be loaded on to a Q-SEPHAROSE® anion exchange chromatography column. Appropriate chromatography resins can also be utilized in "batch" techniques, wherein the resin is contained in a receptacle such as a flask or vessel.

In certain embodiments the FX can be stored after purification (prior to activation).

In certain embodiments comprising dry storage of the FX, the FX can be resuspended prior to the activation step.

In embodiments, any suitable form of FX, for example purified or isolated FX, can be activated by the methods described herein.

Production of FXa

Following elution, the purified or partially purified FX can be loaded onto a chromatographic resin, for example an on exchange resin. In an embodiment the purified FX can be loaded onto an anion exchange resin, for example a strong anion exchange resin, using a loading buffer. In an embodiment the strong anion exchange resin is Q-SEPHAROSE® Fast Flow. In certain embodiments this loading can result in the FX binding to the anion exchange resin. In certain embodiments the pH of the loading buffer can be, for example, 6, 7, 8, 9, 10, 11, or more, or the like. In some embodiments the pH of the loading buffer can be, for example between 6 and 9, or between 7 and 8, or the like. In an embodiment the pH of the loading buffer is 8 at 25° C.

In some embodiments a loading step can comprise equilibrating the chromatography resin with a loading buffer having a conductivity of between 1 and 10 mS/cm, or between 2 and 8 mS/cm, or between 3 and 6 mS/cm, or the like. In certain embodiments the conductivity of the loading buffer can be, for example, 4 mS/cm, or 5 mS/cm, or 6 mS/cm, or 7 mS/cm, or 8 mS/cm, or 9 mS/cm, or 10 mS/cm, or 11 mS/cm, or 12 mS/cm, or the like. In an embodiment the conductivity of the loading buffer is 7 mS/cm at 25° C.

In certain embodiments a loading buffer can comprise a divalent cation. In embodiments the divalent cation can be $Ca^{2+}$, $Mg^{2+}$, $Zn^{2+}$, or the like. In certain embodiments the concentration of the divalent cation in the buffer can be between 1 and 50 mM, or 2 and 40 mM, or 3 and 30 mM, or 4 and 20 mM, or 5 and 15 mM, or 10 and 12 mM, or the like. In embodiments the concentration of the divalent cation in the buffer can be 5 mM, or 6 mM, or mM, or 8 mM, or 9 mM, or 10 mM, or 11 mM, or 12 mM, or 13 mM, or 14 mM, or 15 mM, or the like. In an embodiment the loading buffer comprises $Ca^{2+}$ at a concentration of 2.5 mM. In certain embodiments the targeted resin load is between 5 and 25 mg FX/mL resin, or between 10 and 20 mg/mL, or between 15 and 18 mg/mL, or between 14 and 16 mg/mL resin. In embodiments the targeted resin load is between 0.1 and 5 mg/mL, or 0.5 and 2 mg/mL. In embodiments the targeted resin load is between 0.1 and 1 mg/mL; for example 0.5 mg/mL.

In some embodiments, following the loading step the bound FX is washed with a wash buffer at a pH of about 8. The wash step can comprise multiple column volumes (CVs) of wash buffer, for example, 2, 3, 4, 5, 6, 7, 8, 9, or 10 CVs of wash buffer. In certain embodiments the conductivity of the wash buffer can be, for example, 1 mS/cm, or 2 mS/cm, or 3 mS/cm, or 4 mS/cm, or 5 mS/cm, or 6 mS/cm, or 7 mS/cm, or 8 mS/cm, or 9 mS/cm, or the like.

In an embodiment the conductivity of the wash buffer can be 4 mS/cm at 25° C. In certain embodiments the conductivity of the wash buffer can be, for example, between 0.5 mS/cm and 7 mS/cm, or between 1 mS/cm and 6 mS/cm, or between 2 mS/cm and 5 mS/cm, or between 3 mS/cm and 4 mS/cm, or the like.

In various embodiments a wash buffer can comprise a divalent cation. In some embodiments the divalent cation can be $Ca^{2+}$, $Mg^{2+}$, $Zn^{2+}$, or the like. In embodiments the concentration of the divalent cation in the wash buffer can be between 0.1 and 50 mM, or 0.2 and 40 mM, or 0.3 and 30 mM, or 0.4 and 20 mM, or 0.5 and 15 mM, or 1 and 12 mM, or the like. In embodiments the concentration of the divalent cation in the was buffer can be 0.5 mM, or 0.6 mM, or 0.7 mM, or 0.8 mM, or 0.9 mM, or 1 mM, or 1.1 mM, or 1.2 mM, or 1.3 mM, or 1.4 mM, or 1.5 mM, or the like. In an embodiment the wash buffer can comprise $Ca^{2+}$ at a concentration of 1 mM.

Following the wash step, the FX can remain bound to the chromatographic resin for a contact period. In certain embodiments, during the contact period FX auto-activates, producing FXa. In some embodiments the contact period can be at least 1 hour, or at least 2 hours, or at least 3 hours, or at least 4 hours, or at least 5 hours, or at least 6 hours, or at least 7 hours, or at least 8 hours, or at least 9 hours, or at least 10 hours, or at least 11 hours, or at least 12 hours, or at least 13 hours, or at least 14 hours, or at least 15 hours, or at least 16 hours, or at least 17 hours, or at least 18 hours, or at least 19 hours, or at least 20 hours, or at least 21 hours, or at least 22 hours, or at least 23 hours, or at least 24 hours, or at least 25 hours, or at least 26 hours, or more, or the like. In certain embodiments the contact period can be between 1 and 5 hours, or 2 and 6 hours, or 3 and 7 hours, or 4 and 8 hours, or 5 and 9 hours, or 6 and 10 hours, or 7 and 11 hours, or 8 and 12 hours, or 9 and 13 hours, or 10 and 14 hours, or 11 and 15 hours, or 12 and 16 hours, or 13 and 17 hours, or 14 and 18 hours, or 15 and 19 hours, or 16 and 20 hours, or 17 and 21 hours, or 18 and 22 hours, or 19 and 23 hours, or 20 and 24 hours, or the like.

Following the contact period, the FXa can be eluted from the column using an elution buffer. In certain embodiments the elution buffer can comprise a divalent cation or a counter-ion or both. In certain embodiments the divalent cation can be $Ca^{2+}$, $Mg^{2+}$, $Zn^{2+}$, or the like. In embodiments the counter-ion can be, for example, chloride, or acetate, or sulfate, or phosphate, or the like. In some embodiments the concentration in the elution buffer of the divalent cation or counter-ion can vary over time, for example the concentration can increase over time. For example, in some embodiments the concentration of the divalent cation can increase steadily or in a stepwise fashion from 1-40 mM, or 1-30 mM, or 1-20 mM, or 1-15 mM, or 1-10 mM, or 1-9 mM, or 1-8 mM, or 1-7 mM, or 1-6 mM, or 1-5 mM, or the like. In an embodiment the concentration of the divalent cation can increase in a stepwise fashion from 1-10 mM. In certain embodiments the concentration of the counter-ion can increase steadily or in a stepwise fashion from 1-300 mM, or 2-280 mM, or 3-260 mM, or 4-240 mM, or 6-230 mM, or 7-220 mM, or 8-215 mM, or 9-200 mM, or 10-180 mM, or 11-160 mM, or 12-140 mM, or 13-120 mM, or 14-100 mM, or 15-80 mM, or 16-60 mM, or 17-40 mM, or 20-30 mM, or the like. In an embodiment the concentration of the counter-ion can increase in a stepwise fashion from 9-200 mM. In embodiments the pH of the elution buffer can be, for example, 6, 7, 8, 9 10, or more, or the like. In an embodiment the pH of the elution buffer can be 8. In some embodiments the elution buffer can have a conductivity of between 10 and 100 mS/cm at 25° C., or between 20 and 90 mS/cm, or between 30 and 80 mS/cm, or between 40 and 70 mS/cm, or between 50 and 60 mS/cm, or the like. In an embodiment the elution buffer has a conductivity of between 50 and 60 mS/cm. The eluted FXa can be collected in fractions, which can be tested for the presence and activity of FXa.

In certain embodiments the methods disclosed herein are performed between 8° C. and 30° C., however certain disclosed embodiments can be practiced at other temperatures. In embodiments the methods disclosed herein are performed at a temperature of greater than 8° C., for example at 22° C. to 25° C., 20° C. to 25° C., 18° C. to 22° C., 16° C. to 25° C., 20° C. to 25° C., or the like.

Certain embodiments disclosed here specifically exclude the use of enzymes bound to chromatography resins.

Certain embodiments disclosed here specifically exclude the addition of exogenous enzymes in the activation process.

FXa

Embodiments disclosed herein include activated FX, for example FXa made by a process disclosed herein.

EXAMPLES

The following non-limiting examples are provided for illustrative purposes only in order to facilitate a more complete understanding of representative embodiments. These examples should not be construed to limit any of the embodiments described in the present specification.

Example 1

Recombinant Factor X (rFX)-expressing cell lines were developed in the CHO—S cell line using a plasmid vector harboring a human FX encoding cDNA and a neomycin resistance gene for antibiotic selection. rFX producing cell clones were isolated by limited dilution cloning, and transfected with a vector encoding the endopeptidase furin. Furin-transfected cells producing rFX were cloned a second time. Producer clones were selected based on growth parameters, and productivity of rFX at high activity after activation by extrinsic tenase and Russell's viper venom (RVV), and activated by the extrinsic pathway in a clotting assay in FX-deficient plasma (prothrombin time (PT) clotting assay). Protein quality was verified by measuring impurities by a chromogenic assay specific for FXa, and by sodium-dodecylsulfate polyacrylamide gel electrophoresis (SDS-PAGE) for undercarboxylated rFX, unprocessed rFX forms (single-chain or propeptide containing), and degradation products. A clone meeting all quality criteria was used to produce rFX in a 10 L bioreactor in commercially available POWERCHO™ (a trademark of Lonza Group, Basel Switzerland) media, and supernatant harvests were done periodically over 48 hrs by collecting flow out from the fermenter.

The cell free culture supernatant was loaded onto an anion exchange column (Q-SEPHAROSE®) under neutral pH conditions and a conductivity of about 10-15 mS/cm (25° C.). The column load applied was about 1.5 mg FX antigen per ml of resin. After loading was completed, the resin was washed with 5 CV of an acidic wash buffer (pH=6.0) with a conductivity of about 19 mS/cm (25° C.). The product was subsequently eluted with a elution buffer containing 10 mM Calcium and having a pH of about 8.0 (25° C.) and a conductivity of about 19 mS/cm (25° C.). The product was collected in a volume of 5 CV. The flow rates applied were >50 cm/h for ail steps and the process temperature was 2-8° C.

The purified FX preparation was loaded over 20 hours onto a strong anion exchange column (Q-SEPHAROSE® FF or POROS® [a registered trademark of Life Technologies, Grand Island NY] 50 HQ) at a conductivity of about 7 mS/cm (25° C.) and a pH of about 8 (25° C.). The targeted column load was in a range of 2-10 mg FX/ml resin.

During loading the calcium concentration was about 2.5 mM, and the NaCl concentration was 40 mM. After loading, the column was washed with 5 CV of a wash buffer with a conductivity of about 4 mS/cm (25° C.), a pH of 8.0, and a calcium concentration of 1 mM. The elution was performed using a simultaneous stepwise increase of the $Ca^{2+}$ concentration in the elution buffer from 1 to 10 mM, and the NaCl concentration from 9 to 200 mM at a conductivity of about 24 mS/cm (25° C.) and a pH of 8. All steps were performed at a linear flow rate of 37 cm/h at a resin bed height of about 10 cm. The temperature for activation was room temperature (20-25° C.).

The load and eluate pool fractions were subjected to analytical testing. In Table 3 the volumes and amounts of rFX loaded onto the columns, and the activation times on the columns are listed. Both products from each sample from the activation step were analyzed by a FX chromogenic assay with RVV activation to measure total amount of eluted FX plus FXa in the sample, and by an FXa-specific chromogenic assay to measure FXa selectively. Contents of FXa in percent of total FX present after activation were calculated, and are listed also in Table 3. Samples after one-step purification and after activation were also analyzed by SDS-PAGE. Electrophoresis patterns are shown in FIG. 1.

In conclusion, activation of FX to FXa was successful by this procedure for both samples, and FXa yields were both about 5% FXa of total FX eluted. Although 5-times more rFX was loaded to generate sample number 1-8 than for sample number 1-4, the absolute and relative amounts of FX and FXa in the eluate were similar for both samples. A band with similar size as the heavy chain from plasma-derived FXaα can be seen in the electropherograms of both activated samples. It can be seen that this band compared to the band corresponding to FXaβ was present as the major FXa form.

Table 3: Data from the two samples generated by FX activation: shown are amounts of FX loaded based on antigen and activity measured by ELISA and PT clotting assays, and contact times on the activation column. Also shown are amounts of total FX/FXa measured in the eluate, and of FXa only. Yields of FXa were calculated in percent of total FX/FXa.

FIG. 1 shows SDS-PAGE of FX samples: shown are the rFX start material for activation (lane "rFX"), sample numbers 1-4 and 1-8 containing rFXa after the activation step (lanes "rFX+rFXa #1-4" and "rFX+rFXa #1-8"), and plasma-derived (pd) FXa (lane "pdFXa"). After electrophoresis, protein bands were made visible by Coomassie staining. In the leftmost lane, a molecular weight marker is shown. Bands corresponding to FX and FXa are marked.

Example 2

Recombinant Factor X (rFX)-expressing cell lines are developed in the BHK cell line using a plasmid vector harboring a human FX encoding cDNA and a neomycin resistance gene for antibiotic selection. rFX producing cell clones are isolated by limited dilution cloning, and transfected with a vector encoding the endopeptidase furin. Furin-transfected cells producing rFX are cloned a second time. Producer clones are selected based on growth parameters, and productivity of rFX at high activity after activation by extrinsic tenase and RVV, and activated by the extrinsic pathway in a clotting assay in FX-deficient plasma (pro-thrombin time (PT) clotting assay). Protein quality is verified by measuring impurities by a chromogenic assay specific for FXa, and by SDS-PAGE for undercarboxylated rFX, unprocessed rFX forms (single-chain or propeptide containing), and degradation products. A clone meeting all quality criteria is used to produce rFX in a 100 L bioreactor in commercially available media, and supernatant harvests are performed periodically over 72 hrs by collecting flow out from the bioreactor.

The culture supernatant is loaded onto a hydrophobic interaction column (TOYOPEARL® SuperButyl-550) at a pH of 5.0 and a conductivity of about 35 mS/cm (at 25° C.). The column load applied is about 1.5 mg FX antigen per ml of resin. After loading is completed, the resin is washed with 5 CV of a wash buffer (pH=5.0) with a conductivity of about 35 mS/cm (25° C.). The FX is subsequently eluted with an elution buffer containing 10 mM Calcium and having a pH of about 8.0 (25° C.) and a conductivity of about 10 mS/cm (25° C.). The product is collected in a volume of 8 CV.

The purified FX preparation is loaded onto a strong anion exchange column (Q-SEPHAROSE® FF or POROS® 50 HQ) at a conductivity of about 7 mS/cm (25° C.) and a pH of about 8 (25° C.). The targeted column load is in a range of 2-10 mg FX/ml resin.

During loading the calcium concentration is about 2.5 mM. After loading the column is washed with 7 CV of a wash buffer with a conductivity of about 6 mS/cm (at 25° C.), a pH of 8.2, and a calcium concentration of 1 mM. The FX is contacted with the resin for 10 hours prior to elution.

The elution is performed using a simultaneous stepwise increase of $Ca^{2+}$ concentration in the elution buffer from 1 to 10 mM, and the NaCl counter-ion concentration is increased from 9 to 165 mM at a conductivity of about 20 mS/cm (at 25° C.) and a pH of 8. All steps are performed at a linear flow rate of 50 cm/h at a resin bed height of about 15 cm. The temperature for activation is room temperature (20-25° C.).

TABLE 3

| | | LOAD | | | | ELUATE | | |
| --- | --- | --- | --- | --- | --- | --- | --- | --- |
| Sample ID | Column type | Volume of FX loaded until max. column capacity achieved [mL] | FX loaded according to ELISA [µg] | FX loaded according to PT clotting [µg] | Contact time on column [h] | FX/FXa amount RVV assay [µg] | FXa amount FXa assay [µg] | % FXa in the FX/FXa mix |
| #1-4 | AEX on Q-SEPHAROSE ® FF (GE Healthcare) | 20 | 993 | 744 | 20 | 702 | 35 | 5.0 |
| #1-8 | POROS ® (Applied Biosystems) | 100 | 4967 | 3722 | 20 | 732 | 42 | 5.7 |

Example 3

Recombinant Factor)((rFX)-expressing cells lines are developed from a 293 cell line using a plasmid vector harboring a human FX encoding cDNA and an ampicillin resistance gene for antibiotic selection. rFX producing cell clones are isolated by limited dilution cloning, and transfected with a vector encoding the endopeptidase furin. Furin-transfected cells producing rFX are cloned a second time. Producer clones are selected based on standard growth parameters as well as productivity of rFX at high activity after activation by extrinsic tenase and RVV, and activated by the extrinsic pathway in a clotting assay in FX-deficient plasma (prothrombin time (PT) clotting assay). Protein quality is verified by measuring impurities by a chromogenic assay specific for FXa, and by SDS-PAGE for undercarboxylated rFX, unprocessed rFX forms (single-chain or propeptide containing), and degradation products. A clone meeting all quality criteria is used to produce rFX in a 50 L bioreactor in commercially available media, and supernatant harvests are performed periodically over 36 hrs by collecting flow from the bioreactor.

The cell-free culture supernatant is loaded onto a hydrophobic resin (TOYOPEARL® [a registered trademark of Tosoh Bioscience, Belgium] SuperButyl-550) using a "batch" technique at a pH of 5.0 and a conductivity of about 35 mS/cm (at 25° C.). The protein load applied is about 1.5 mg FX antigen per ml of resin. After loading is completed, the resin is washed using a wash buffer (pH=5.0) with a conductivity of about 35 mS/cm (25° C.). The FX is subsequently eluted from the resin with an elution buffer containing 10 mM Calcium and having a pH of about 8.0 (25° C.) and a conductivity of about 10 mS/cm (25° C.).

The recovered FX is then lyophilized with the following components in the stated ratio:

100 ug FX/30 mg glycine 120 mg NaCl/10 mg HEPES,

After storage −70° C. for two months, the FX is reconstituted and loaded onto a strong anion exchange column (Q-SEPHAROSE® FF or POROS® 50 HQ) at a conductivity of about 8 mS/cm (25° C.) and a pH of about 8.1 (25° C.). The targeted column load is in a range of 2-10 mg FX/ml resin.

During loading the calcium concentration is about 2.5 mM. The FX is contacted with the resin for 16 hours prior to elution.

The elution is performed using a simultaneous stepwise increase of $Ca^{2+}$ concentration in the elution buffer from 2.5 to 20 mM, and the NaCl counter-ion concentration is increased from 9 to 250 mM at a conductivity of about 30 mS/cm (at 25° C.) and a pH of 8.5. All steps are performed at a linear flow rate of 20 cm/h at a resin bed height of about 25 cm. The temperature for activation is room temperature (20-25° C.).

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present disclosure, which is defined solely by the claims. Accordingly, embodiments of the present disclosure are not limited to those precisely as shown and described.

Certain embodiments are described herein, including the best mode known to the inventor for carrying out the methods and devices described herein, Of course, variations on these described embodiments will become apparent to those of ordinary skill in the art upon reading the foregoing description. Accordingly, this disclosure includes all modifications and equivalents of the subject matter recited in the claims appended hereto as permitted by applicable law. Moreover, any combination of the above-described embodiments in all possible variations thereof is encompassed by the disclosure unless otherwise indicated herein or otherwise clearly contradicted by context.

Groupings of alternative embodiments, elements, or steps of the present disclosure are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the disclosure are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope otherwise claimed. No language in the present specification should be construed as indicating any non-claimed element essential to the practice of embodiments disclosed herein.

The invention claimed is:

1. A method for activating Coagulation Factor X (FX) comprising:
    a) providing an aqueous solution that comprises FX isolated from mammalian plasma or tissue culture cell supernatant;
    b) contacting the aqueous solution with an anion-exchange material under binding conditions for a contact period of at least five hours; and
    c) eluting the activated FX (FXa) from the anion-exchange material with an elution buffer.

2. The method of claim 1, wherein the contact period is at least 10 hours.

3. The method of claim 1, wherein the binding conditions comprise a conductivity of 8 mS/cm or less.

4. The method of claim 1, wherein the binding conditions comprise a pH of between 8 and 10.

5. The method of claim 1, wherein the FX is loaded at greater than 0.5 mg per mL of anion-exchange material.

6. The method of claim 1, wherein the contact and eluting steps are performed at a temperature of greater than 8° C.

7. The method of claim 1, wherein the elution buffer comprises at least one of a divalent cation and a counter-ion.

8. The method of claim 7, wherein the divalent cation is $Ca^{2+}$.

9. The method of claim 7, wherein the counter-ion is at least one of chloride, acetate, or sulfate.

10. The method of claim 7, wherein the concentration of the divalent cation or counter-anion or both in the elution buffer increases over time.

11. The method of claim 10, wherein the concentration of the divalent cation increases from 1 to 100 mM.

12. The method of claim 10, wherein the concentration of the divalent cation increases from 1 to 10 mM.

13. The method of claim 10, wherein the concentration of the counter-anion increases from 1 to 1000 mM.

14. The method of claim 10, wherein the concentration of the counter-anion increases from 9 to 200 mM.

15. The method of claim 1, wherein the elution buffer has a conductivity between 1 and 100 mS/cm at 25° C.

16. The method of claim 1, wherein the aqueous solution comprising FX is contacted with the anion-exchange material in the presence of ethylenediaminetetraacetic acid (EDTA).

17. The method of claim 1, wherein the anion-exchange material comprises a ligand comprising at least one of quaternary ammonium [Q], diethylaminoethyl [DEAE], diethylaminopropyl [ANX], or primary amine.

18. The method claim 1, wherein the anion-exchange material comprises a matrix derived from at least one of polystyrene, polymethylmetaacrylate, polyvinylbenzene, polyvinyl pyridine, cross-linked poly(styrene-divinylbenzene), sepharose, and cross linked agarose.

19. The method of claim 1, further comprising, prior to step a), isolating FX from mammalian plasma to produce the aqueous solution.

20. The method of claim 1, further comprising, prior to step a), isolating FX from tissue culture cell supernatant to produce aqueous solution.

21. The method of claim 1, wherein the FX in the aqueous solution is isolated by precipitation, ultrafiltration, or chromatography.

* * * * *